United States Patent
Haidacher et al.

(10) Patent No.: US 10,918,439 B2
(45) Date of Patent: Feb. 16, 2021

(54) METHOD AND DEVICE FOR DETERMINING GEOMETRIC PARAMETERS FOR TOTAL KNEE REPLACEMENT SURGERY

(71) Applicant: Brainlab AG, Munich (DE)

(72) Inventors: Florian Haidacher, Neubeuern (DE); Timo Neubauer, Neukeferloh (DE); Mario Schubert, Poing (DE)

(73) Assignee: BRAINLAB AG, Munich (DE)

( * ) Notice: Subject to any disclaimer, the term of this patent is extended or adjusted under 35 U.S.C. 154(b) by 110 days.

(21) Appl. No.: 15/569,820

(22) PCT Filed: Apr. 28, 2015

(86) PCT No.: PCT/EP2015/059202
§ 371 (c)(1),
(2) Date: Oct. 27, 2017

(87) PCT Pub. No.: WO2016/173626
PCT Pub. Date: Nov. 3, 2016

(65) Prior Publication Data
US 2018/0132937 A1 May 17, 2018

(51) Int. Cl.
*G06K 9/00* (2006.01)
*A61B 34/10* (2016.01)
(Continued)

(52) U.S. Cl.
CPC .......... *A61B 34/10* (2016.02); *A61B 17/155* (2013.01); *A61B 17/157* (2013.01);
(Continued)

(58) Field of Classification Search
None
See application file for complete search history.

(56) References Cited

U.S. PATENT DOCUMENTS

| 4,841,975 A | 6/1989 | Woolson |
| 6,711,432 B1 * | 3/2004 | Krause ................ A61B 17/15 |
| | | 128/922 |

(Continued)

FOREIGN PATENT DOCUMENTS

| EP | 1563799 A1 | 8/2005 |
| EP | 1939569 A1 | 6/2008 |

(Continued)

OTHER PUBLICATIONS

European Patent Office, International Search Report and Written Opinion corresponding to PCT/EP2015/059202, dated Jul. 2, 2015. No. of pp. 10. NL.

*Primary Examiner* — Shervin K Nakhjavan
(74) *Attorney, Agent, or Firm* — Tucker Ellis LLP (57) ABSTRACT

The present invention relates to a data processing method performed by a computer, for determining geometric parameters of a phantom leg bone using a cutting guide that defines a cutting plane and that is configured to abut a predetermined surface section of the phantom leg bone. The method comprises acquiring cutting guide position data describing the spatial position of the cutting guide, acquiring relative position data describing the spatial position of a first mechanical axis point relative to the predetermined surface section of the phantom leg bone, and determining, based on the cutting guide position data and the relative position data, first axis point position data describing the spatial position of the first mechanical axis point of the phantom leg bone. The present invention further relates to a corresponding cutting guide and a corresponding computer program and computer.

18 Claims, 5 Drawing Sheets

(51) Int. Cl.
  *A61B 17/15* (2006.01)
  *G06T 7/00* (2017.01)
  *G06T 7/60* (2017.01)
  *A61B 90/00* (2016.01)
  *A61B 34/20* (2016.01)
  *A61B 17/17* (2006.01)

(52) U.S. Cl.
  CPC .............. *G06T 7/0016* (2013.01); *G06T 7/60* (2013.01); *A61B 17/1703* (2013.01); *A61B 17/1764* (2013.01); *A61B 2034/108* (2016.02); *A61B 2034/2055* (2016.02); *A61B 2090/3937* (2016.02); *G06T 2207/10081* (2013.01); *G06T 2207/10088* (2013.01); *G06T 2207/10104* (2013.01); *G06T 2207/10132* (2013.01); *G06T 2207/30008* (2013.01)

(56) References Cited

U.S. PATENT DOCUMENTS

| | | | |
|---|---|---|---|
| 8,990,052 B2* | 3/2015 | Lavallee | G06F 17/50 703/1 |
| 2002/0133175 A1* | 9/2002 | Carson | A61B 90/10 606/130 |
| 2003/0100907 A1* | 5/2003 | Rosa | A61B 17/155 606/86 R |
| 2003/0212403 A1 | 11/2003 | Swanson | |
| 2004/0068187 A1* | 4/2004 | Krause | A61B 17/15 600/443 |
| 2005/0096535 A1* | 5/2005 | de la Barrera | A61B 17/155 600/424 |
| 2005/0113846 A1* | 5/2005 | Carson | A61F 2/461 606/130 |
| 2005/0234332 A1* | 10/2005 | Murphy | A61B 5/4528 600/426 |
| 2005/0267358 A1 | 12/2005 | Tuma et al. | |
| 2006/0015120 A1* | 1/2006 | Richard | A61B 90/06 606/102 |
| 2006/0122491 A1* | 6/2006 | Murray | A61B 17/157 600/414 |
| 2006/0195111 A1 | 8/2006 | Couture | |
| 2006/0235290 A1* | 10/2006 | Gabriel | A61B 17/157 600/407 |
| 2006/0271056 A1* | 11/2006 | Terrill-Grisoni | A61B 17/025 606/84 |
| 2007/0100258 A1* | 5/2007 | Shoham | A61B 17/157 600/587 |
| 2008/0051798 A1* | 2/2008 | Colquhoun | A61B 17/1764 606/87 |
| 2008/0269596 A1* | 10/2008 | Revie | G06Q 10/087 600/424 |
| 2009/0005783 A1 | 1/2009 | Gotte et al. | |
| 2009/0131941 A1* | 5/2009 | Park | A61B 17/154 606/87 |
| 2009/0216113 A1* | 8/2009 | Meier | A61B 17/32 600/424 |
| 2009/0222014 A1* | 9/2009 | Bojarski | A61B 17/155 606/88 |
| 2010/0063508 A1 | 3/2010 | Borja et al. | |
| 2010/0234850 A1* | 9/2010 | Dees, Jr. | A61B 17/155 606/87 |
| 2011/0029116 A1* | 2/2011 | Jordan | A61B 17/155 700/98 |
| 2011/0196377 A1* | 8/2011 | Hodorek | A61B 17/155 606/87 |
| 2011/0208093 A1 | 8/2011 | Gross et al. | |
| 2011/0257653 A1* | 10/2011 | Hughes | A61B 34/10 606/79 |
| 2012/0330135 A1 | 12/2012 | Millahn et al. | |
| 2013/0066319 A1* | 3/2013 | Aram | A61B 34/10 606/60 |
| 2013/0144392 A1* | 6/2013 | Hughes | A61B 17/157 623/18.11 |
| 2014/0022599 A1 | 1/2014 | Sugino | |
| 2014/0106926 A1 | 4/2014 | Hagedorn | |
| 2014/0200902 A1* | 7/2014 | Aram | A61B 34/10 705/2 |
| 2016/0089153 A1* | 3/2016 | Couture | A61B 17/155 606/88 |
| 2017/0042557 A1* | 2/2017 | Plaskos | A61B 17/155 |

FOREIGN PATENT DOCUMENTS

| | | |
|---|---|---|
| EP | 2008597 A1 | 12/2008 |
| WO | 2006060631 A1 | 6/2006 |
| WO | 2014045119 A2 | 3/2014 |

* cited by examiner

METHOD AND DEVICE FOR DETERMINING GEOMETRIC PARAMETERS FOR TOTAL KNEE REPLACEMENT SURGERY

RELATED APPLICATION DATA

This application is a national phase application of International Application No. PCT/EP2015/059202 filed Apr. 4, 2015, published in the English language.

The present invention relates to a data processing method, performed by a computer, for determining geometric parameters of a phantom leg bone using a cutting guide, and to a corresponding cutting guide, a cutting guide set and a computer program.

In the context of knee replacement surgery, it is important to know the mechanical axis of the leg bones. This mechanical axis is important for diagnostic purposes as well as for preparing surgical steps. The mechanical axis can for example be a reference for a cutting plane, preparatory for performing a cut for implanting an artificial replacement. The mechanical axis is particularly important with reference to the tibia and the femur.

The use of cutting guides which are positioned relative to the bone to be cut is widely known in the prior art.

Document US 2010/063508 discloses systems and methods for joint replacement. The systems and methods include a surgical orientation device and at least one orthopedic fixture. The surgical orientation device and orthopedic fixtures can be used to locate the orientation of an axis in the body, to adjust an orientation of a cutting plane or planes along a bone surface, to distrackt a joint, or to otherwise assist in an orthopedic procedure or procedures.

Document US 2011/208093 discloses systems and methods for joint replacement. The systems and methods include a surgical orientation device, a reference sensor device, an at least one orthopedic fixture. The surgical orientation device, reference sensor device, and orthopedic fixtures can be used to locate the orientation of an axis in the body, to adjust an orientation of a cutting plane or planes along a bone surface, or otherwise to assist in an orthopedic procedure(s).

Document US 2014/0225999 discloses a method and a device for determining the mechanical axis of a bone using an electronic device which is rigidly attached to the bone and comprises a video camera.

The present invention provides an improved method and an improved device for determining geometric parameters of a phantom leg bone, wherein the geometric parameters can be determined more easily, faster and less prone to errors.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The inventive data processing method is performed in connection with a trackable cutting guide that defines a cutting plane and that is configured to abut a predetermined surface section of a phantom leg bone, wherein the method comprises the following steps:

acquiring cutting guide position data describing the spatial position of the cutting guide;

acquiring, from an anatomical atlas or from an image of the phantom patient, relative position data describing the spatial position of a first mechanical axis point relative to the predetermined surface section of the phantom leg bone;

determining, based on the cutting guide position data and the relative position data, first axis point position data describing the spatial position of the first mechanical axis point of the phantom leg bone.

In the context of the present invention, the described data processing method is suitable to be used for training purposes and may therefore be performed for determining geometric parameters of an artificial leg bone, also known as a phantom leg bone, or even a leg bone of a dead human being. In the following, the term "phantom" will be used for a physical artificial model of a patient or body parts thereof, or a dead human being or body parts thereof.

It is further important to note that the inventive method makes use of an external data source such as an anatomical atlas or images of a patient, which provides further data which is not provided by the cutting guide but is necessary for determining the geometric parameters of the phantom leg bone.

With the present invention, the registration process of known knee replacement procedures which require a registration of the patient anatomy with a pointer device to get navigation information, is simplified by substituting the registration by evaluating the position of the cutting guide on the one hand and the size of the patient anatomy, for example the length of the phantom tibia or phantom femur bone on the other hand.

In particular, the cutting guide position data can be provided by a medical tracking system determining the spatial position of the cutting guide, for example via at least one tracking marker coupled to the cutting guide.

In this context, the cutting guide can be provided with at least one tracking marker that in turn can be detected by a medical tracking system, for example an EM-tracking system or an optical tracking system, so that the position (location and/or alignment) of the cutting guide within the three-dimensional space is known.

For example, the at least one tracking marker can be releasably attached to the cutting guide, so that it can be removed again after the geometric parameters of the phantom leg bone have been determined.

Moreover, the relative position data can be acquired from an anatomical patient atlas, wherein acquiring may comprise the following steps:

acquiring anatomical conditions data describing anatomical conditions of the specific phantom leg bone, such as gender or age of a phantom patient, or the length of the phantom leg bone;

acquiring, based on the anatomical conditions data, model data describing the geometry of an atlas leg bone model that matches the phantom leg bone;

determining, based on the model data, relative position data of the specific phantom leg bone.

Since the cutting guide's spatial position alone is not sufficient to determine the position of the first mechanical axis point of the phantom leg bone, further data has to be acquired from another data source which may be an anatomical atlas of the patient. As will be described later on, such atlas may describe a general three-dimensional shape of the leg bone. For this reason, the general model has to be scaled and adapted to the actual phantom leg bone. According to the present invention, such adaption may be based on a determination of anatomical conditions of the actual phantom leg bone such as the size or the length of the actual phantom leg bone. Moreover, further anatomical conditions may be entered to match the general to the actual phantom leg bone. For example, the gender of the phantom patient can be entered so that the system may provide a general female or a general male model of the phantom leg bone.

Further, the bone length may in turn be determined by measuring the relative position of the cutting guide and a second mechanical axis point of the phantom leg bone, wherein the cutting plane defined by the cutting guide may comprise the first mechanical axis point.

As an alternative to an anatomical atlas as a second data source, data as to the relative position of the first mechanical axis point and the predetermined surface section of the phantom leg bone can be acquired from a patient image, particularly from an X-ray-image that has been taken. In case the direction from which a two-dimensional patient image has been taken as well as the scale of the image relative to the real leg bone, for example the ratio between the number of image pixels and the distance in reality is known, the distance between the predetermined surface section and the mechanical axis point which may be manually set by medical personnel or automatically by a computer, can be easily determined and scaled to the actual phantom leg bone.

Moreover, the inventive data processing method can be used to determine the spatial position of the mechanical axis of a phantom leg bone. Therefore, the method may comprise the step of:
  acquiring second axis point position data describing the spatial position of a second mechanical axis point of the phantom leg bone, being spaced apart from the first mechanical axis point;
  determining, based on the first axis point position data and the second axis point position data, mechanical axis position data describing the spatial position of the mechanical axis of the phantom leg bone.

With the position of two points of the mechanical axis of the phantom leg bone known, the mechanical axis running through both of these points can be calculated.

In the following, more specific procedures according to the present invention are described, which may be performed on a phantom tibia on the one hand, and a phantom femur on the other hand:

In case the inventive data processing method is performed on a phantom tibia, the second axis point position data may be acquired via at least one tracking marker tracked by the medical tracking system, which is coupled to the phantom tibia at a predetermined spatial position relative to the second axis point, for example at at least one malleolus of the phantom tibia. The tracking markers can be coupled to the tibia in any suitable manner, for example by adhesive means. In this context, the cutting guide may be an extramedullar cutting guide and may abut the phantom tibia at the anterior tibia cortex. In case additional parameters are taken from a patient image instead of a patient atlas, the patient image, for example an X-ray patient image may be taken from a medial-lateral direction.

It is also conceivable that the inventive data processing method is performed on a phantom femur. In that case, the second axis point position data may be acquired via pivoting the phantom femur around the center of the femur head, wherein the femur head may constitute the second mechanical axis point. Moreover, the cutting guide may be coupled to the phantom femur during this pivoting procedure, and may be tracked by the medical tracking system. Further, the cutting guide attached to the phantom femur may be an intramedullar cutting guide and may abut the phantom femur at the most distal condyle point of the phantom femur. In case a patient image, for example an X-ray patient image is used as a further data source, the image may be taken from an anterior-posterior direction.

Moreover, the step of acquiring relative position data may comprise measuring the distance between the first mechanical axis point relative to the predetermined surface section of the phantom leg bone. In case geometric parameters of a phantom tibia have to be acquired, the distance in a direction which may be approximately perpendicular to the mechanical axis of the phantom tibia and relative to the anterior tibia cortex may be measured. More specifically, the distance in an anterior-posterior direction may be measured, wherein this direction may further be defined by the cutting guide. For example, the cutting guide or the cutting block of the cutting guide may be provided with a marking that should be brought into alignment with the actual anterior-posterior direction by medical personnel. In case geometric data of a phantom femur has to be acquired, the distance between the first mechanical axis point and the most distal condyle point in a direction parallel to the anatomical axis of the phantom femur may be measured.

With the methods described above, the position of the mechanical axis of a phantom femur or a phantom tibia can be determined. In total knee replacement surgery, it is however important to know the position of the mechanical axis of both, the tibia and the femur, so that the inventive method may comprise determining the first axis points of the mechanical axes for both, the phantom tibia and the corresponding phantom femur.

The present invention further relates to a trackable cutting guide configured to assist in determining geometric parameters of a leg bone, wherein the cutting guide defines a cutting plane and is configured to abut a predetermined surface section of the leg bone, and wherein the cutting guide is provided with at least one tracking marker in a fixed spatial position with respect to the cutting plane.

For example, the cutting guide may be a disposable article configured to be attached to a lower leg of a patient, for example to a patient tibia or to a patient femur.

It is also conceivable that the inventive cutting guide is used for training purposes on a phantom lower leg, particularly on a phantom tibia or a phantom femur. The same applies to the computer program described further below, which may be used for an actual surgery on a living human being or merely for training purposes using a physical artificial leg bone or the bone of a dead human being.

In case the cutting guide is configured to be attached to a femur of a patient, the cutting guide may further comprise an alignment guide which may also be provided with at least one tracking marker. The alignment guide may have a shaft portion, which, as it is introduced into the medullary canal of the phantom femur, defines an anatomical axis of the femur. Moreover, the cutting guide may be slidably supported along the shaft portion of the alignment guide.

The present invention may also provide a cutting guide set for total knee replacement surgery comprising an extramedullar cutting guide as described herein and configured to be attached to a tibia of a patient, an intramedullar cutting guide as described herein, which is configured to be attached to a femur of a patient, and at least one tracking marker that is configured to be attached to a lower leg of a patient, for example at the malleoli of a tibia of a patient.

The present invention also relates to a program which, when running on a computer or when loaded onto a computer, causes the computer to perform the following steps:
acquiring cutting guide position data describing the spatial position of the cutting guide;
acquiring, from an anatomical atlas or from an image of a patient, relative position data describing the spatial position of a first mechanical axis point relative to a predetermined surface section of a leg bone of the patient;
determining, based on the cutting guide position data and the relative position data, first axis point position data describing the spatial position of the first mechanical axis point of the leg bone; and/or a non-transitory, computer-readable program storage medium on which the program is stored in particular in a non-transitory form.

The present invention also concerns a computer, for example a cloud computer, on which the program as described above is stored or run, or which comprises the non-transitory, computer-readable program storage medium as described above.

In the following, technical terms and expressions used within the present documents are explained and defined in the following:

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer as described above, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a tracking marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape. Additionally or alternatively, flat tracking markers showing geometrical shapes which are easily detectable by an optical tracking system (as shown in the figures) may be used as well.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the data processing method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The inventive principle further allows to provide information about the orientation of the mechanical tibia axis relative to the mechanical femur axis, which is defined by the varus/valgus angle between the tibia axis and the femur axis in a projection onto the frontal plane on the one hand, and by the angle between the tibia axis and the femur axis in a projection onto the sagittal plane on the other hand.

In order to verify a correct alignment of the mechanical axes of the tibia and the femur for a trial implant, tracking markers can be attached to the maleolli points of the tibia as described further above, so as to determine the position of the distal axis point of the tibia. Moreover, a trial knee implant may be provided with an interface for a further tracking marker which will allow to calculate a proximal axis point of the tibia as well as a distal axis point of the femur. The proximal axis point of the femur can be determined by pivoting the femur around the femur head centre.

With this procedure, the relative position of the mechanical axis of the femur and the mechanical axis of the tibia can be determined for a positioned trial implant.

In the following, the invention is described with reference to the enclosed figures which represent preferred embodiments of the invention. The scope of the invention is not however limited to the specific features disclosed in the figures, which show.

Figure 1:
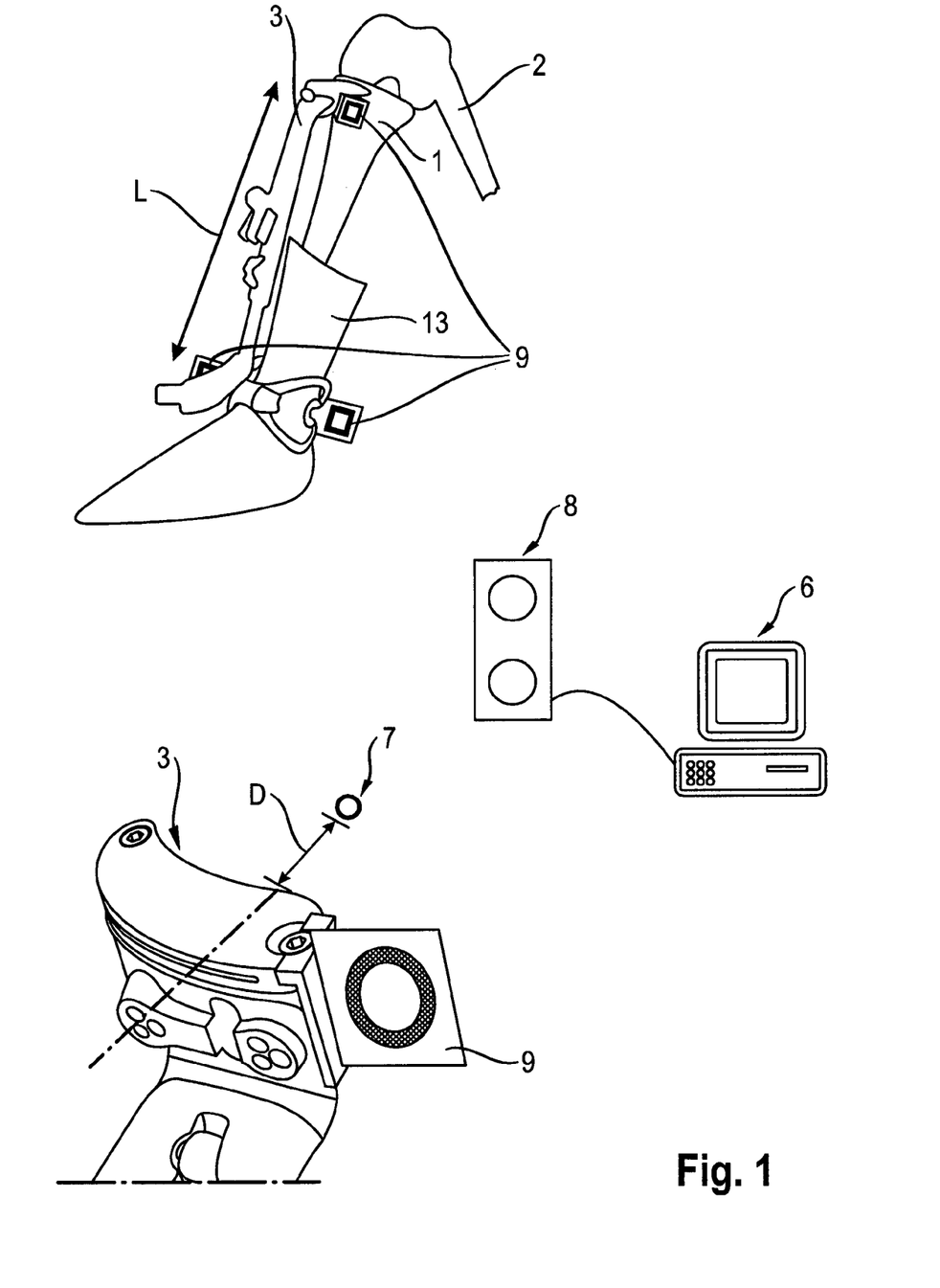
FIG. 1 an extramedullar, trackable cutting guide according to the present invention attached to a phantom tibia, FIG. 2 an intramedullar, trackable cutting guide attached to a phantom femur, FIG. 3 an overview of the geometric parameters determined according to the present invention, FIG. 4 a phantom lower leg comprising a phantom tibia and a phantom femur and the mechanical axes thereof, FIG. 5 an overview over the crucial steps of the inventive method.

FIG. 1 shows an extramedullar cutting guide 3 which defines a cutting plane 4 (please refer to FIG. 3) for the proximal end of a phantom tibia 1. The cutting guide 3 is attached to the phantom tibia via a distal clamp and abuts the phantom tibia 1 at the anterior tibia cortex 5 (please refer to the left side of FIG. 3). The length of the cutting guide 3 can be adapted to the length of the phantom tibia 1.

The proximal section (cutting block) of the cutting guide 3 is provided with a tracking marker 9 so that the spatial position of both, the cutting guide 3 and the cutting block can be determined via a medical tracking system 8 that is connected to a computer 6 of a medical navigation system. The cutting guide 3 defines a cutting plane 4 which comprises the first mechanical axis point 7 of the phantom tibia 1. The cutting block of the cutting guide 3 comprises a visible marker line which indicates the anterior-posterior direction within which the distance D between the first mechanical axis point 7 and the anterior tibia cortex 5 contacting the cutting block of the cutting guide 3 has to be determined.

For this purpose, the length of the phantom tibia is determined via a measurement of the distance between the tracking marker 9 attached to the cutting block and two further tracking markers 9 which have been adhesively attached to the distal malleoli of the phantom tibia 1 which define a second mechanical axis point 10 of the phantom tibia 1.

With the length L of the phantom tibia 1 known, an atlas can provide a bone model which matches the phantom tibia 1, and from which further geometric parameters such as the distance D between the anterior tibia cortex 5 and the first mechanical axis point 7 in an anterior-posterior direction can be determined.

With the help of the anatomical atlas, the exact position of the first mechanical axis point 7 with respect to the phantom tibia 1 can be calculated. The mechanical axis 11 of the phantom tibia 1 can be also calculated, since it runs through the first mechanical axis point 7 indicated by the first tracking marker 9 attached to the cutting block, and through the second mechanical axis point 10 which is indicated by the two further tracking markers 9 attached to the distal malleoli of the phantom tibia 1.

The position of the mechanical axis 11 of the phantom femur 2 can be calculated in a similar manner.

Figure 2:
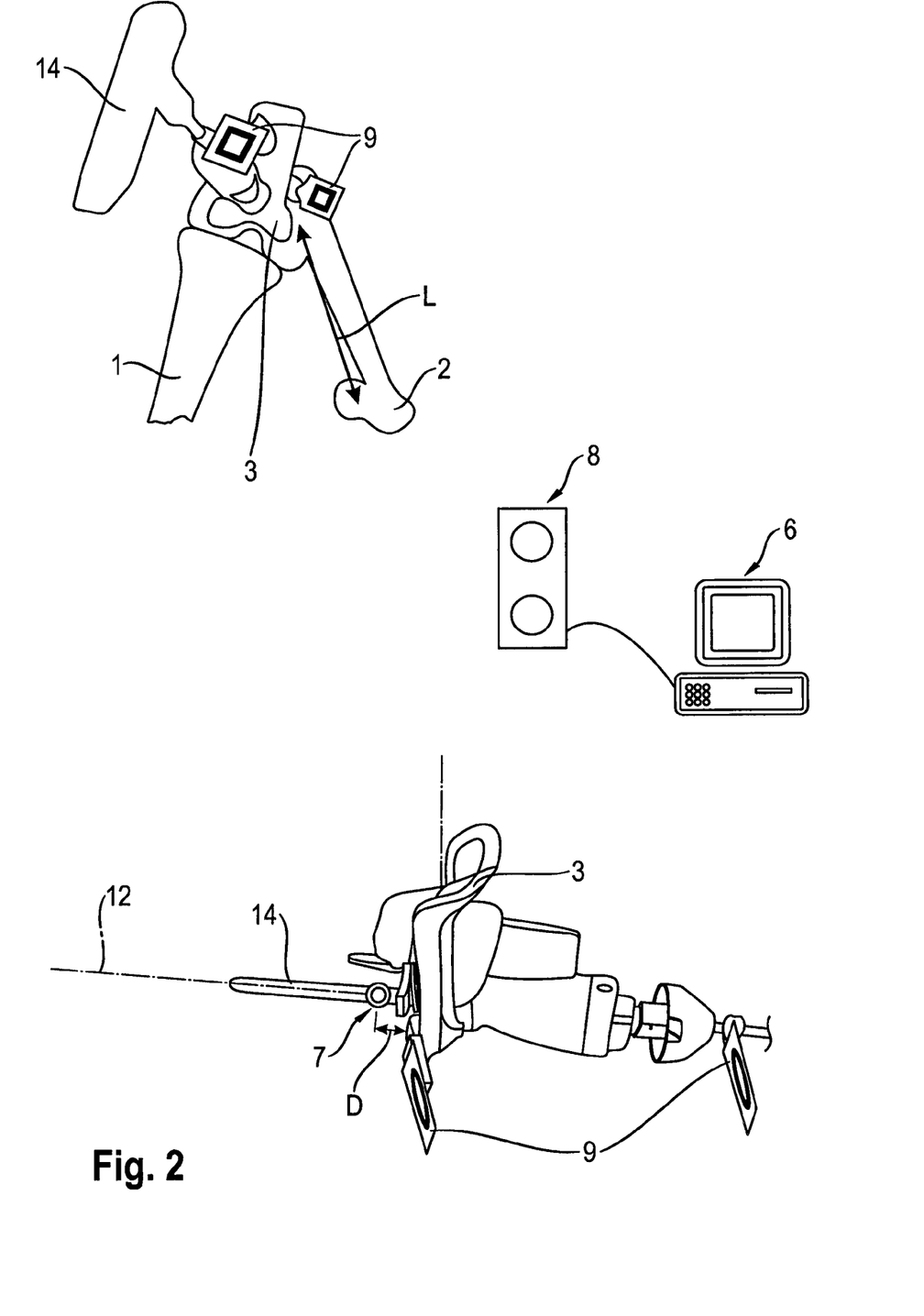

FIG. 2 shows a cutting guide 3 comprising an alignment guide 14 which is configured to be introduced into the medullar canal of a phantom femur 2. The anatomical axis 12 of the phantom femur 2 is therefore defined by the alignment guide 14.

The second axis point 10 of the phantom femur 2 (please refer to the right side of FIG. 3), which is constituted by the pivotal center of femur head, can be determined by pivoting the phantom femur 2 around the femur head, wherein the tracking markers 9 attached to the cutting guide 3 are tracked by means of the medical tracking system 8. The cutting guide 3 also comprises a marking which indicates the anterior-posterior direction (dashed line in FIG. 2).

The first mechanical axis point 7 of the phantom femur 2 is determined by tracking the cutting guide 3 via the tracking markers 9. The distance D between the first mechanical axis point 7 and the most distal condyle point 5 (please refer to the right side of FIG. 3) at which the cutting guide 3 abuts the phantom femur 2 can be determined with the help of the anatomical atlas.

To obtain the geometric model matching the phantom femur 2 from the atlas, the length L of the phantom femur 2 may be calculated from the distance between the second mechanical axis point 10 (center of the femur head) and the most distal condyle point 5 of the phantom femur 2.

As soon as a matching model of the phantom femur 2 is obtained from the atlas, the distance D in the direction of the anatomical axis 12 (indicated by the tracking marker 9 attached to the alignment guide 14) of the phantom femur 2 is known, which in turn allows calculating the spatial position of the first mechanical axis point 7.

Figure 3:
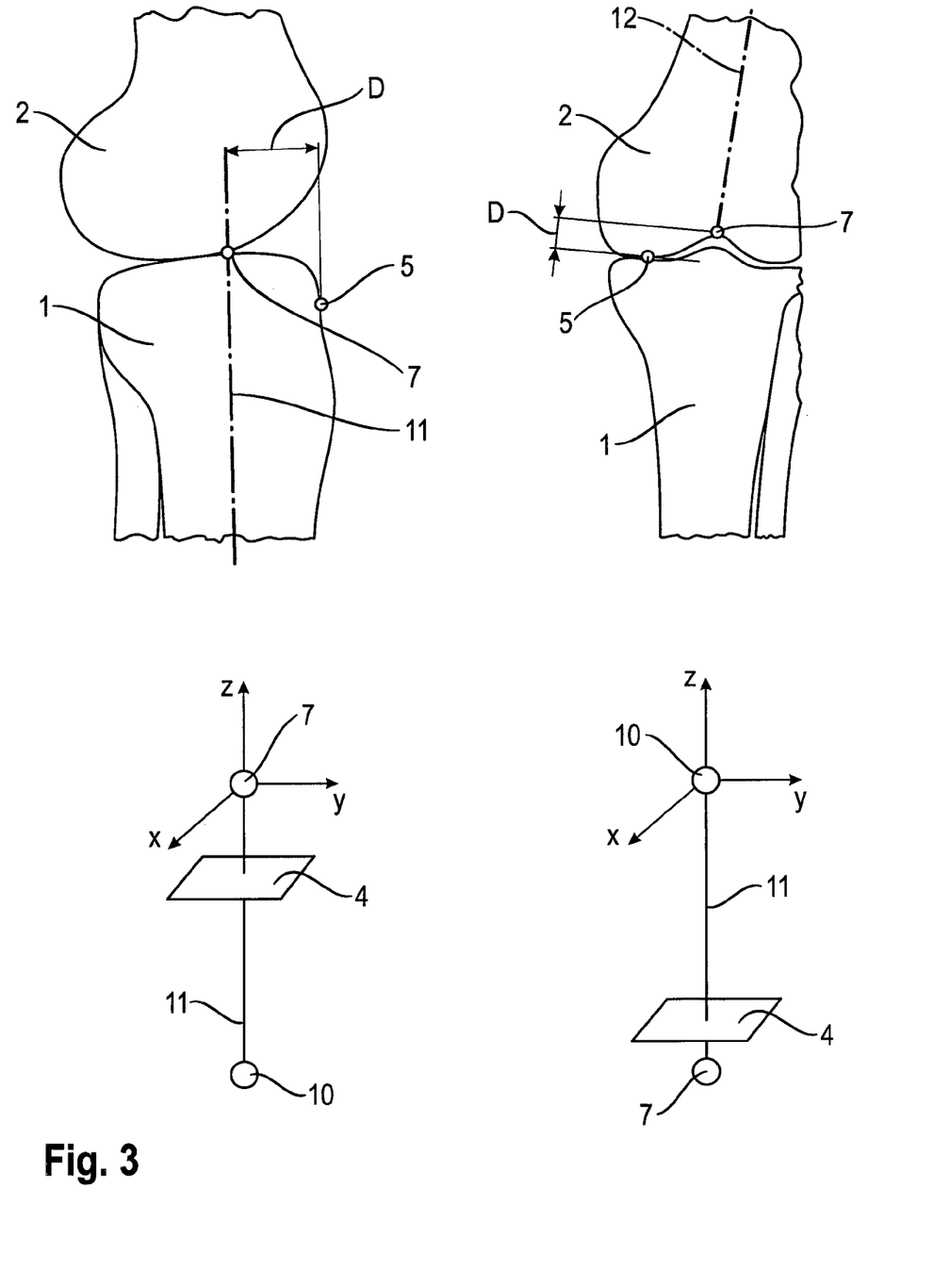

FIG. 3 shows the geometric parameters obtained with the inventive method, wherein the parameters for the phantom tibia 1 are shown on the left side and the parameters for the phantom femur 2 are shown on the right side. Both, the phantom tibia 1 and the phantom femur 2 have a mechanical axis 11 which runs through a first mechanical axis point 7. In case of the tibia 1, the mechanical axis point 7 is spaced from the anterior tibia cortex 5 in a direction perpendicular to the mechanical axis 11 by a distance D. In case of the femur 2, the first mechanical axis point 7 is spaced from the most distal condyle point 5 of the phantom femur in a direction parallel to the anatomical axis 12 of the phantom femur 2 by another distance D.

Both distances D can either be taken from an anatomical atlas, or can be set manually by medical personnel or automatically by a computer within an image data set of the patient, for example a two-dimensional X-ray image taken from a known direction.

For both, the tibia 1 and the femur 2 a second mechanical axis point 10 is determined as described above, which allows to calculate the mechanical axis 11 of the phantom femur 2 and the mechanical axis 11 of the phantom tibia 1.

It can also be seen in FIG. 3 that in both cases, the cutting plane 4 defined by the cutting guide 3 has a specific position (location and/or alignment) with respect to the mechanical axis points 7 and 10 and relative to the mechanical axes 11.

Figure 4:
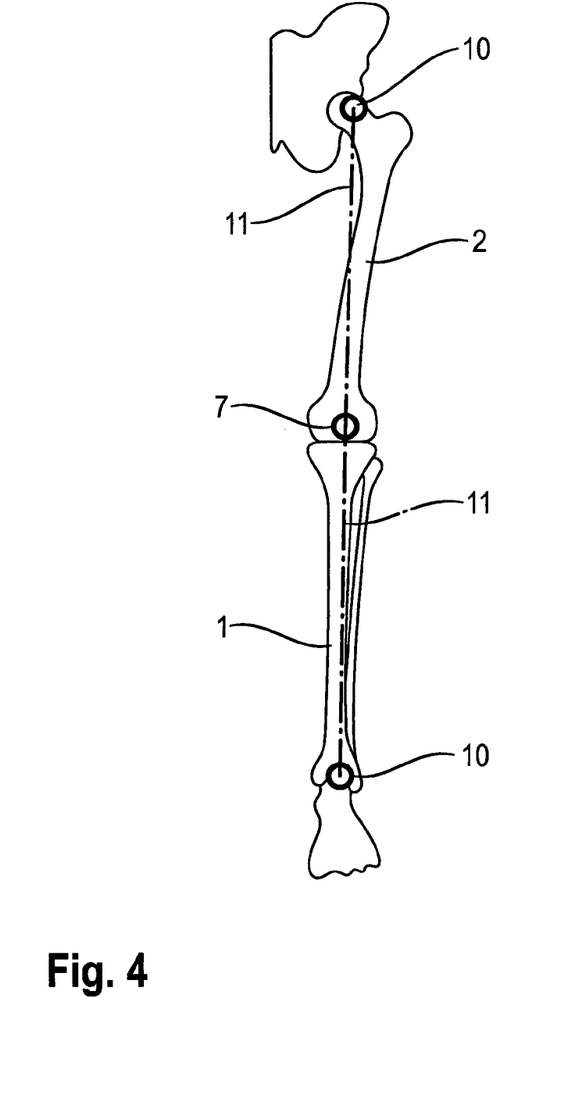

For total knee replacement surgery, the mechanical axes 11 (please refer to FIG. 4) of both, a phantom tibia 1 and a phantom femur 2 can be determined with the invention as described herein.

Figure 5:
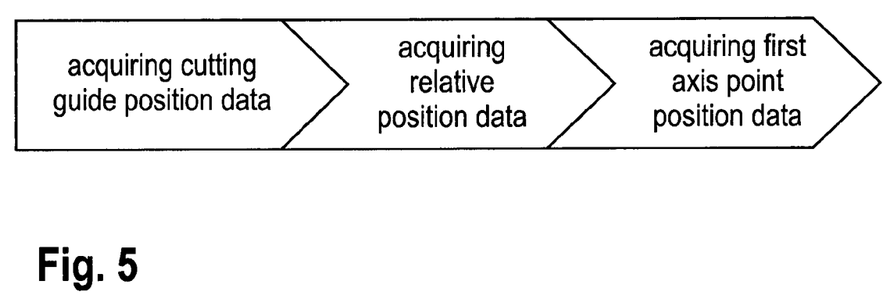

FIG. 5 shows the crucial steps of the inventive data processing method, wherein the cutting guide position data is acquired by tracking the cutting guide 3 with a medical tracking system 8 and the position of the first mechanical axis point 7 with respect to the cutting guide is acquired with the help of an anatomical atlas or a patient image indicating its position relative to the cutting guide. With this data known, it is then possible to calculate the absolute position of the first mechanical axis point 7 within space and relative to a phantom leg bone 1, 2.

The invention claimed is:

1. A method for determining geometric parameters of a leg bone using an extramedullar cutting guide having a cutting block at a proximal portion thereof, the cutting block including a passage adapted to receive a cutting tool and defining a cutting plane, wherein the cutting block is configured to directly contact a predetermined surface section of the leg bone, the method comprising:
    acquiring cutting guide position data describing the spatial position of the cutting guide when the cutting block has been brought into direct contact with the predetermined surface section;
    acquiring, from an anatomical atlas or from at least one image of a patient, relative position data describing the spatial position of a first mechanical axis point relative to the predetermined surface section; and
    determining, based on the cutting guide position data and the relative position data, first axis point position data describing the spatial position of the first mechanical axis point of the leg bone.

2. The method according to claim 1, wherein the cutting guide position data is provided by a medical tracking system determining the spatial position of the cutting guide.

3. The method according to claim 2, wherein the medical tracking system determines the spatial position of the cutting guide via at least one tracking marker coupled to the cutting guide.

4. The method according to claim 1, wherein acquiring the relative position data from an anatomical atlas comprises:
    acquiring anatomical conditions data describing anatomical conditions of the leg bone;
    acquiring, based on the anatomical conditions data, model data describing the geometry of an atlas leg bone model that matches the leg bone;
    determining, based on the model data, relative position data of the specific leg bone.

5. The method according to claim 4, wherein acquiring anatomical conditions data comprises determining the length (L) of the leg bone by determining the relative position of the cutting guide and a second mechanical axis point of the leg bone.

6. The method according to claim 4, wherein the anatomical conditions data describing anatomical conditions of the leg bone is on of gender or age of a patient, or the length (L) of the leg bone.

7. The method according to claim 1, wherein acquiring said relative position data from the at least one image of the patient comprises determining, within the patient image, the relative position of the surface section and the first mechanical axis point which is set within the at least one image of the patient.

8. The method according to claim 1, further comprising the steps of:
    acquiring second axis point position data describing the spatial position of a second mechanical axis point of the leg bone, being spaced apart from the first mechanical axis point;
    determining, based on the first axis point position data and the second axis point position data, mechanical axis position data describing the spatial position of the mechanical axis of the leg bone.

9. The method according claim 8, wherein the leg bone is a tibia, and wherein the second axis point position data is acquired via at least one tracking marker tracked by the medical tracking system, which is coupled to the tibia at a predetermined spatial position relative to the second axis point; and/or the patient image is taken from a medial-lateral direction.

10. The method according to claim 9, wherein acquiring relative position data comprises measuring the distance (D) between the first mechanical axis point relative to the predetermined surface section of the leg bone in a direction approximately perpendicular to the mechanical axis of the tibia and relative to the anterior tibia cortex.

11. The method according to claim 9, wherein the medical tracking system is coupled to the tibia at least one malleolus of the tibia.

12. The method according to claim 1, wherein the first axis point or a mechanical axis is determined for both, a tibia and a corresponding femur.

13. The method of claim 1, comprising:
generating user interface control data from the determined first axis point position data describing the spatial position of the first mechanical axis point of the leg bone.

14. The method of claim 13, comprising:
controlling a user interface to provide the user interface control data to an associated user as information.

15. A non-transitory machine readable storage medium having instructions stored thereon that when executed cause a system to perform the steps comprising:
acquiring cutting guide position data describing the spatial position of the cutting guide when the cutting guide has been brought into direct contact with the predetermined surface section;
acquiring, from an anatomical atlas or from an image of a patient, relative position data describing the spatial position of a first mechanical axis point relative to a predetermined surface section of a leg bone of the patient;
determining, based on the cutting guide position data and the relative position data, first axis point position data describing the spatial position of the first mechanical axis point of the leg bone.

16. A method for determining geometric parameters of a leg bone using an intramedullar cutting guide having an alignment guide which is configured to be introduced into the medullar canal of a femur, the cutting guide defining a cutting plane and being configured to directly contact a predetermined surface section of the leg bone, the method comprising:
acquiring cutting guide position data describing the spatial position of the cutting guide when the cutting guide has been brought into direct contact with the predetermined surface section;
acquiring, from an anatomical atlas or from at least one image of a patient, relative position data describing the spatial position of a first mechanical axis point relative to the predetermined surface section; and
determining, based on the cutting guide position data and the relative position data, first axis point position data describing the spatial position of the first mechanical axis point of the leg bone.

17. The method according to claim 16, wherein
the second axis point position data is acquired via pivoting the femur around the center of the femur head, the femur head center being the second mechanical axis point;
the cutting guide abuts the femur at the most distal condyle point of the femur; and/or
the patient image is taken from an anterior-posterior direction.

18. The method according to claim 17, wherein acquiring relative position data comprises measuring the distance (D) between the first mechanical axis point relative to the predetermined surface section of the leg bone in a direction parallel to the anatomical axis of the femur and relative to the most distal condyle point.

* * * * *